United States Patent [19]

Miyazawa et al.

[11] Patent Number: 4,886,622
[45] Date of Patent: Dec. 12, 1989

[54] OPTICALLY ACTIVE LIQUID CRYSTAL COMPOUND HAVING CYANO GROUP

[75] Inventors: Kazutoshi Miyazawa; Takashi Inukai; Hiromichi Inoue; Shinichi Saito; Kouji Ohno, all of Kanagawa, Japan

[73] Assignee: Chisso Corporation, Ohsaka, Japan

[21] Appl. No.: 086,584

[22] Filed: Aug. 18, 1987

[30] Foreign Application Priority Data

Aug. 18, 1986 [JP] Japan ................. 61-192516

[51] Int. Cl.$^4$ .................. G02F 1/13; C09K 19/30; C09K 19/34; C09K 19/46; C09K 19/20; C09K 19/12; C07C 121/75; C07C 239/30

[52] U.S. Cl. .................. 252/299.61; 252/299.01; 252/299.5; 252/299.63; 252/299.65; 252/299.66; 252/299.67; 350/350 R; 350/350 S; 544/296; 544/298; 544/316; 544/318; 544/333; 544/334; 544/335; 546/255; 546/258; 546/257; 546/261; 546/264; 546/300; 546/330; 546/339; 558/419; 558/420; 558/423; 558/425

[58] Field of Search .......... 252/299.01, 299.5, 299.61, 252/299.63, 299.65, 299.66, 299.67; 350/350 R, 350 S; 558/419, 420, 425, 423; 544/296, 316, 318, 298, 333, 334, 335; 546/255, 257, 258, 261, 264, 300, 330, 339

[56] References Cited

U.S. PATENT DOCUMENTS

| | | | |
|---|---|---|---|
| 4,110,243 | 8/1978 | Arnick et al. | 252/299.67 |
| 4,149,413 | 4/1979 | Gray et al. | 252/299.66 |
| 4,225,736 | 11/1980 | Beguin et al. | 252/299.65 |
| 4,287,085 | 9/1981 | Takei et al. | 252/299.67 |
| 4,311,610 | 1/1982 | Zaschke et al. | 252/299.61 |
| 4,341,652 | 7/1982 | Takei et al. | 252/299.87 |
| 4,622,165 | 11/1986 | Kano et al. | 252/299.65 |
| 4,689,176 | 8/1987 | Inoue et al. | 252/299.65 |
| 4,728,458 | 3/1988 | Higuchi et al. | 252/299.65 |
| 4,737,313 | 4/1988 | Saito et al. | 252/299.63 |
| 4,780,242 | 10/1988 | Miyazawa et al. | 252/299.65 |
| 4,818,432 | 4/1989 | Miyazawa et al. | 252/299.66 |
| 4,820,839 | 4/1989 | Krause et al. | 252/299.61 |
| 4,828,754 | 5/1989 | Takehara et al. | 252/299.65 |

FOREIGN PATENT DOCUMENTS

| | | | |
|---|---|---|---|
| 156726 | 10/1985 | European Pat. Off. | 252/299.65 |
| 188222 | 7/1986 | European Pat. Off. | 252/299.65 |
| 211646 | 2/1987 | European Pat. Off. | 252/259.65 |
| 3525015 | 1/1986 | Fed. Rep. of Germany | 252/299.65 |
| 3515373 | 11/1986 | Fed. Rep. of Germany | 252/299.61 |
| 3518734 | 11/1986 | Fed. Rep. of Germany | 252/299.61 |
| 3706766 | 9/1987 | Fed. Rep. of Germany | 252/299.63 |
| 60-78972 | 5/1985 | Japan | 252/299.61 |
| 61-122250 | 6/1986 | Japan | 252/299.65 |
| 62-22889 | 1/1987 | Japan | 252/299.61 |
| 63-130574 | 6/1988 | Japan | 252/299.65 |
| WO86/00067 | 1/1986 | World Int. Prop. O. | 252/299.61 |
| WO86/07055 | 12/1986 | World Int. Prop. O. | 252/299.61 |
| WO87/01717 | 2/1987 | World Int. Prop. O. | 252/299.63 |
| WO87/05013 | 8/1987 | World Int. Prop. O. | 252/299.65 |

OTHER PUBLICATIONS

Furukawa, K. et al., Ferroelectrics, vol. 85, pp. 451–459 (1988).
Coates, D., Liquid Crystals, vol. 2, No. 4, pp. 423–428 (1987).
Dubois, J. C. et al., Mol. Cryst. Liq. Cryst., vol. 42, No. 1-3, pp. 139–152 (1977).
Gray, G. W. et al., Liquid Crystals & Plastic Crystals, vol. 1, pp. 142–143, John Wiley & Sons, Inc., N.Y. (1974).

Primary Examiner—Teddy S. Gron
Attorney, Agent, or Firm—Wenderoth, Lind & Ponack

[57] ABSTRACT

An optically liquid crystalline compound having an extremely large spontaneous polarization value and a chiral smectic liquid crystal composition containing the compound are provided, the compound being expressed by the formula

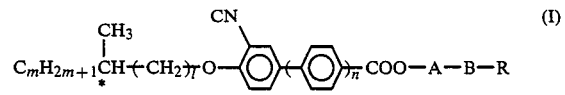

wherein m represents an integer of 2 to 18; l represents an integer of 0 to 12; n represents 0 or 1; R represents an alkyl group or an alkoxy group each of 2 to 20 carbon atoms, a halogen atom or cyano group; and A and B each represent a single bond,

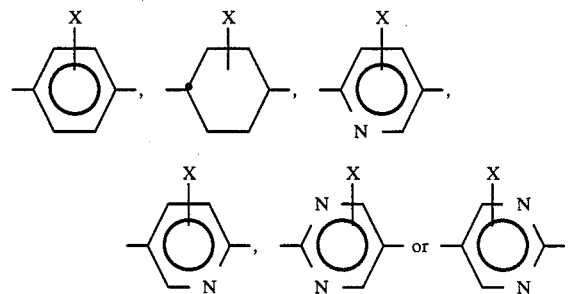

wherein X represents hydrogen atom, a halogen atom or cyano group, and a chiral smectic liquid crystal composition containing at least one kind of the above compound.

13 Claims, No Drawings

OPTICALLY ACTIVE LIQUID CRYSTAL COMPOUND HAVING CYANO GROUP

BACKGROUND OF THE INVENTION

1. Field of the Invention

This invention relates to novel liquid crystalline compounds and liquid crystal compositions containing the same. More particularly it relates to liquid crystalline compounds having an optically active group and a chiral liquid crystal composition containing the same.

The liquid crystalline compounds defined in the present application include not only compounds for which it is possible to observe their crystalline state by themselves, but also compounds for which it is impossible to observe their crystalline state, but nevertheless have a chemical structure similar to those of liquid crystal compounds and also have properties useful as a constituent of liquid crystal compositions.

2. Description of the Related Art

At present, TN (Twisted Nematic) mode display has been most broadly employed for liquid crystal elements, but this mode is inferior in the aspect of response rate to emissive mode display elements such as electroluminescent display, plasma display, etc. Thus, various attempts in this respect have been made, but nevertheless a possibility of improvement to a large extent does not seem to have been achieved. Thus, various attempts for obtaining a liquid crystal display device based on another principle, in place of TN mode display elements have been made. As one of such attempts, there is a display mode making use of ferroelectric liquid crystals (N.A. Clark et al: Applied Phys. lett., 36, 899 (1980)). This mode makes use of ferroelectric liquid crystal chiral smectic C phase (hereinafter abbreviated to SC* phase) or chiral smectic H phase (hereinafter abbreviated to SH*), and has the following three superior specific feature as compared with TN mode display:

The first specific feature is that the display elements have a very high response rate which amounts to 100 times those of TN mode display elements.

The second specific feature is that the elements have a memory effect so that the multiplex drive is easy in combination with the above high rate response properties.

The third specific feature is that by only by adjusting the reverse time of polarity, it is possible to easily obtain the gray scale as compared with TN type display mode, and hence the display mode has been considered to be suitable for graphic display.

However, in spite of such superior specific features thereof, satisfactory results have not yet been obtained in the aspect of response rate in the case of currently known ferroelectric liquid crystals and compositions and hence it seems that they have come to a deadlock prior to their practical use. This can be said to be due to the fact that development of compounds having a large spontaneous polarization value (Ps) has been late.

SUMMARY OF THE INVENTION

In view of such a situation, the present inventors have searched for various liquid crystal compounds having an optically active group mainly in order to develop liquid crystal compounds having specific features, particularly those having a large spontaneous polarization value, suitable for being utilized for the above display mode, and as a result have achieved the present invention.

The present invention resides in
an optically active liquid crystalline compound expressed by the formula

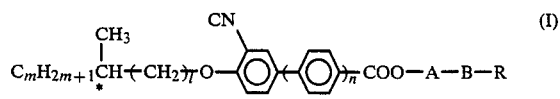

wherein m represents an integer of 2 to 18; l represents an integer of 0 to 12; n represents 0 or 1; R represents an alkyl group or an alkoxy group each of 2 to 20 carbon atoms, a halogen atom or cyano group; and A and B each represent a single bond,

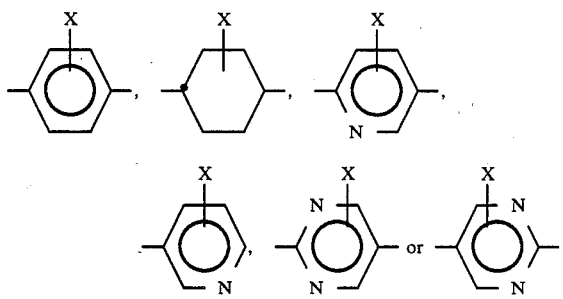

wherein X represents hydrogen atom, a halogen atom or cyano group, and a chiral smectic liquid crystal composition containing at least one kind of the above compounds.

DETAILED DESCRIPTION OF PREFERRED EMBODIMENTS

The phase transition points and the spontaneous polarization values Ps of representative compounds of the formula (I) are shown in Tables 1 and 2.

TABLE 1

| Compound No. | \multicolumn{6}{c}{In formula (I)} | \multicolumn{5}{c}{Phase transition point (°C.)} | | |
|---|---|---|---|---|---|---|---|---|---|---|---|---|
| | l | m | n | A | B | R | C | SE | SC* | SA | Ch | I | Note |
| 1 | 0 | 4 | 1 | Single bond | 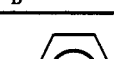 | —OC$_8$H$_{17}$ | • 32.3 | — | • 37.5 | • 97.3 | — | • | |
| 2 | 0 | 4 | 1 | Single bond | 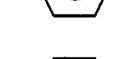 | —OC$_{10}$H$_{21}$ | • 35.4 | — | (• 30.0) | • 99.5 | — | • | |

TABLE 1-continued

| Compound No. | \multicolumn{5}{c}{In formula (I)} | | | | | \multicolumn{5}{c}{Phase transition point (°C.)} | | | | | Note |
|---|---|---|---|---|---|---|---|---|---|---|---|
| | l | m | n | A | B | R | C | SE | SC* | SA | Ch | I | |
| 3 | 0 | 4 | 1 | Single bond | (F-phenyl) | —OC$_6$H$_{13}$ | ● 38.2 | — | (● 50.6) | ● 90.0 | — | ● | |
| 4 | 0 | 4 | 1 | Single bond | (F-phenyl) | —OC$_7$H$_{15}$ | ≦20° C. | — | ●139.0 | — | ●182.3 | ● | |
| 5 | 0 | 6 | 0 | (phenyl) | (phenyl) | —C$_8$H$_{17}$ | ● 54.3 | — | (● 42.5) | ● 73.2 | — | ● | Example 2 |
| 6 | 0 | 6 | 0 | (phenyl) | (phenyl) | —C$_{12}$H$_{25}$ | ● 60.6 | — | ● 70.2 | ● 78.3 | — | ● | |
| 7 | 0 | 6 | 0 | (phenyl) | (phenyl) | —OC$_6$H$_{13}$ | ●103.0 | (● 80.9) | — | ●108.4 | — | ● | Example 1 |
| 8 | 0 | 6 | 0 | (phenyl) | (phenyl) | —OC$_8$H$_{17}$ | ● 67.4 | — | ● 90.0 | ●104.7 | — | ● | |
| 9 | 0 | 6 | 0 | (phenyl) | (phenyl) | —OC$_{11}$H$_{23}$ | ● 74.7 | — | ● 99.6 | ●103.0 | — | ● | |
| 10 | 0 | 6 | 0 | (phenyl) | (phenyl) | —OC$_{12}$H$_{25}$ | ● 78.0 | — | ●100.3 | ●104.5 | — | ● | |
| 11 | 0 | 6 | 0 | (pyrimidinyl) | (phenyl) | —C$_8$H$_{17}$ | ● 68.5 | — | — | (● 58.0) | — | ● | |
| 12 | 0 | 6 | 0 | (pyrimidinyl) | (phenyl) | —OC$_{10}$H$_{21}$ | ● 62.0 | — | ● 75.0 | ● 86.5 | — | ● | |
| 13 | 0 | 6 | 0 | (phenyl) | (pyridinyl) | —φC$_8$H$_{17}$ | ● 70.0 | — | (● 53.5) | ● 61.6) | — | ● | |
| 14 | 0 | 6 | 1 | Single bond | (phenyl) | —φC$_8$H$_{17}$ | ≦20° C. | — | — | ● 62.4 | — | ● | |

TABLE 1-continued

| Compound No. | In formula (I) | | | | | | Phase transition point (°C.) | | | | | | Note |
|---|---|---|---|---|---|---|---|---|---|---|---|---|---|
| | l | m | n | A | B | R | C | SE | SC* | SA | Ch | I | |
| 15 | 0 | 6 | 1 | Single bond | 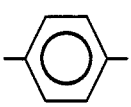 | —OC$_6$H$_{13}$ | ≦20° C. | — | • 41.6 | • 91.3 | — | • | |
| 16 | 0 | 6 | 1 | Single bond | 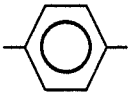 | —OC$_7$H$_{15}$ | ≦20° C. | — | • 54.4 | • 92.8 | — | • | |
| 17 | 0 | 6 | 1 | Single bond | 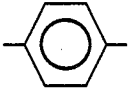 | —OC$_8$H$_{17}$ | • 27.5 | — | • 57.0 | • 94.3 | — | • | Example 3 |
| 18 | 0 | 6 | 1 | Single bond | 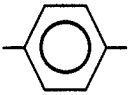 | —OC$_9$H$_{19}$ | • 42.8 | — | • 48.7 | • 90.8 | — | • | |
| 19 | 0 | 6 | 1 | Single bond | 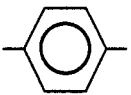 | —OC$_{10}$H$_{21}$ | • 67.8 | — | (• 57.8) | • 98.4 | — | • | |
| 20 | 0 | 6 | 1 | Single bond | 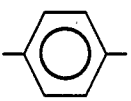 | —OC$_{12}$H$_{25}$ | • 34.5 | — | • 51.0 | • 99.9 | — | • | |
| 21 | 0 | 6 | 1 | Single bond | 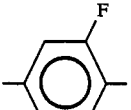 | —OC$_6$H$_{13}$ | ≦20° C. | — | • 58.5 | • 88.3 | — | • | |
| 22 | 0 | 6 | 1 | Single bond | 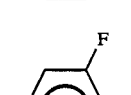 | —OC$_7$H$_{15}$ | ≦20° C. | — | • 64.0 | • 90.2 | — | • | |
| 23 | 0 | 6 | 1 | Single bond | 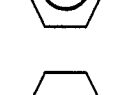 | —C$_5$H$_{11}$ | • 65.4 | — | — | — | — | • | |
| 24 | 0 | 6 | 1 | Single bond | 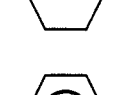 | —CN | •103.0 | — | — | — | — | • | |
| 25 | 0 | 6 | 1 | Single bond | 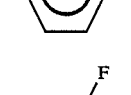 | —CN | • 95.5 | — | — | — | — | • | |
| 26 | 0 | 6 | 1 | | 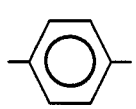 | —C$_8$H$_{17}$ | • 71.0 | — | •130.0 | — | •148.0 | • | |

TABLE 1-continued
| Compound No. | l | m | n | A | B | R | C | SE | SC* | SA | Ch | I | Note |
|---|---|---|---|---|---|---|---|---|---|---|---|---|---|
| 27 | 0 | 6 | 1 | 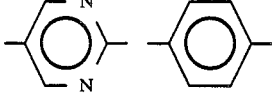 | 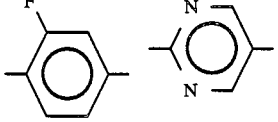 | —$C_8H_{17}$ | ≦20° C. | — | •139.0 | — | •182.3 | • | |
| 28 | 0 | 6 | 1 | 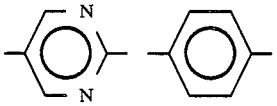 | 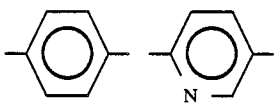 | —$C_8H_{17}$ | • 79.0 | — | • 82.3 | — | •127.2 | • | |
| 29 | 0 | 6 | 1 | 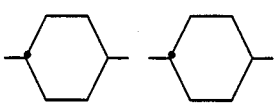 | 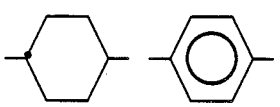 | —$OC_8H_{17}$ | • 50.0 | — | •175.2 | •208.5 | — | • | |
| 30 | 0 | 6 | 1 | 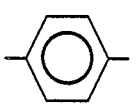 | 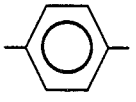 | —$C_8H_{17}$ | • 50.0 | — | •161.3 | — | •166.7 | • | |
| 31 | 0 | 6 | 1 | 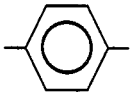 | 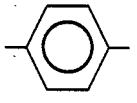 | —$C_3H_7$ | • 48.6 | — | — | •169.2 | •181.0 | • | |
| 32 | 0 | 6 | 1 | 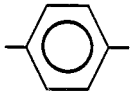 | 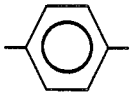 | —$C_5H_{11}$ | • 70.0 | — | — | •176.4 | — | • | |
| 33 | 1 | 2 | 1 | Single bond | 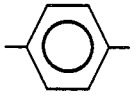 | —$C_6H_{13}$ | • 71.0 | — | (• 43.2) | •129.8 | — | • | |
| 34 | 1 | 2 | 1 | Single bond | | —$C_8H_{17}$ | • 53.0 | — | (• 25.0) | •134.1 | — | • | |
| 35 | 1 | 2 | 1 | Single bond | | —$OC_8H_{17}$ | • 62.4 | — | (• 38.0) | •159.7 | — | • | |
| 36 | 1 | 2 | 1 | Single bond | | —$OC_{12}H_{25}$ | • 36.0 | (• 31.6) | — | •152.4 | — | • | |
| 37 | 5 | 2 | 1 | Single bond | | —$C_3H_7$ | • 95.0 | — | (• 81.7) | •148.4 | — | • | |
| 38 | 5 | 2 | 1 | Single bond | | —$C_4H_9$ | •100.3 | — | •103.3 | •147.2 | — | • | |
| 39 | 5 | 2 | 1 | Single bond | | —$C_7H_{15}$ | • 82.0 | — | •119.5 | •149.8 | — | • | |

TABLE 1-continued
| Compound No. | In formula (I) | | | | | | Phase transition point (°C.) | | | | | | Note |
|---|---|---|---|---|---|---|---|---|---|---|---|---|---|
| | l | m | n | A | B | R | C | SE | SC* | SA | Ch | I | |
| 40 | 5 | 2 | 1 | Single bond |  | —C$_8$H$_{17}$ | • 70.8 | — | •118.8 | •148.4 | — | • | |
| 41 | 5 | 2 | 1 | Single bond |  | —OC$_4$H$_9$ | • 118.2 | — | (• 106.5) | • 176.5 | — | • | |
| 42 | 5 | 2 | 1 | Single bond |  | —OC$_7$H$_{15}$ | • 104.7 | — | • 140.5 | • 170.5 | — | • | |
| 43 | 5 | 2 | 1 | Single bond |  | —OC$_8$H$_{17}$ | • 97.4 | — | • 142.0 | • 170.0 | — | • | |
| 44 | 5 | 2 | 1 | Single bond | 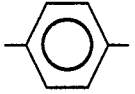 | —OC$_{10}$H$_{21}$ | • 95.8 | — | • 138.1 | • 167.3 | — | • | |
| 45 | 5 | 2 | 1 | Single bond |  | —OC$_{12}$H$_{25}$ | • 90.0 | — | • 142.8 | • 167.1 | — | • | |
| 46 | 5 | 2 | 1 | Single bond | 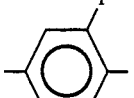 | —OC$_7$H$_{15}$ | • 80.6 | — | • 142.8 | • 167.1 | — | • | |
| 47 | 5 | 2 | 1 | Single bond | 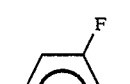 | —CN | • 127.6 | — | — | — | — | • | |
| 48 | 5 | 2 | 1 | 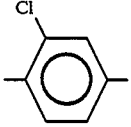 | 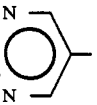 | —C$_8$H$_{17}$ | • 70.0 | — | • 121.1 | — | •156.8 | • | |
| 49 | 5 | 2 | 1 | 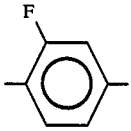 | 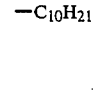 | —C$_{10}$H$_{21}$ | • 80.0 | — | • 199.4 | — | •199.8 | • | |
| 50 | 6 | 2 | 1 | Single bond |  | —C$_8$H$_{17}$ | • 75.2 | — | • 123.1 | • 146.5 | — | • | |
| 51 | 6 | 2 | 1 | Single bond |  | —OC$_8$H$_{17}$ | • 97.9 | — | •143.1 | • 163.8 | — | • | |

TABLE 1-continued

| Compound No. | \multicolumn{5}{c}{In formula (I)} | | | \multicolumn{6}{c}{Phase transition point (°C.)} |
|---|---|---|---|---|---|---|---|---|---|---|---|---|
| | l | m | n | A | B | R | C | SE | SC* | SA | Ch | I | Note |
| 52 | 6 | 2 | 1 | Single bond |  | —OC₁₂H₂₅ | • 86.1 | — | •136.1 | • 162.8 | — | • | |
| 53 | 7 | 2 | 0 | | 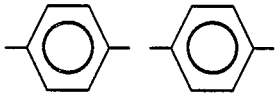 | —C₈H₁₇ | • 91.0 | — | •164.8 | • 168.2 | — | • | |
| 54 | 7 | 2 | 0 | | 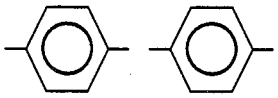 | —OC₇H₁₅ | • 89.5 | — | •166.2 | • 167.7 | — | • | |
| 55 | 7 | 2 | 0 | | 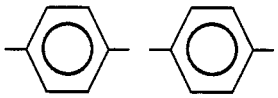 | —OC₈H₁₇ | • 75.6 | — | •143.4 | • 146.1 | — | • | |
| 56 | 7 | 2 | 1 | Single bond |  | —C₂H₅ | • 76.8 | — | — | • 147.0 | — | • | |
| 57 | 7 | 2 | 1 | Single bond |  | —C₄H₉ | • 87.4 | — | • 94.2 | • 148.2 | — | • | |
| 58 | 7 | 2 | 1 | Single bond | 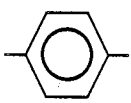 | —C₅H₁₁ | •100.5 | — | •110.2 | • 152.9 | — | • | |
| 59 | 7 | 2 | 1 | Single bond | 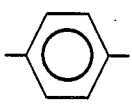 | —C₈H₁₇ | • 88.3 | — | •129.2 | • 150.0 | — | • | |
| 60 | 7 | 2 | 1 | Single bond | 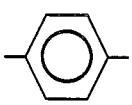 | —C₉H₁₉ | • 81.4 | — | •129.5 | • 148.8 | — | • | |
| 61 | 7 | 2 | 1 | Single bond | 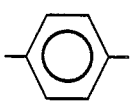 | —OC₂H₅ | • 88.0 | — | — | • 181.4 | — | • | |
| 62 | 7 | 2 | 1 | Single bond | 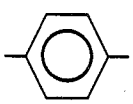 | —OC₄H₉ | •116.4 | — | — | • 178.7 | — | • | |
| 63 | 7 | 2 | 1 | Single bond | 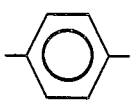 | —OC₅H₁₁ | •113.0 | — | •125.9 | • 174.6 | — | • | |
| 64 | 7 | 2 | 1 | Single bond | 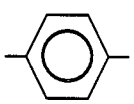 | —OC₈H₁₇ | • 99.8 | — | • 147.1 | • 167.2 | — | • | |

TABLE 1-continued

| Compound No. | In formula (I) | | | | | | Phase transition point (°C.) | | | | | | Note |
|---|---|---|---|---|---|---|---|---|---|---|---|---|---|
| | l | m | n | A | B | R | C | SE | SC* | SA | Ch | I | |
| 65 | 7 | 2 | 1 | Single bond | phenyl | —OC$_{12}$H$_{25}$ | • 89.2 | — | • 145.6 | • 164.0 | — | • | |
| 66 | 7 | 2 | 1 | Single bond | phenyl | —OC$_{14}$H$_{29}$ | • 84.2 | — | • 138.6 | • 158.6 | — | • | |
| 67 | 7 | 2 | 1 | Single bond | phenyl | —CN | • 129.4 | — | — | (• 124.7) | — | | |

TABLE 2

| Compound No. | Spontaneous polarization value PS (nC/cm$^2$) | |
|---|---|---|
| 5 | 236.0 | (67.2° C.)[2] |
| 7 | 226.6[*1] | (82.2° C.) |
| 17 | 240.0 | (27.0° C.) |
| 21 | 302.1 | (48.5° C.) |
| 26 | 198.2 | (100.0° C.) |
| 27 | 221.8 | (109.0° C.) |
| 28 | 165.5 | (52.3° C.) |
| 29 | 217.1 | (145.2° C.) |

[*1]Extrapolation values sought from values obtained by mixing the respective compounds with a liquid crystal having smectic C phase but exhibiting no spontaneous polarization, the extrapolation values being the minimum values which the compounds have latently.
[*2]( ) shows a measuring temperature.

The first specific feature of the compounds expressed by the formula (I) is that their spontaneous polarization values are very large. It is known that ferroelectric liquid crystals are higher in the response rate, i.e., a rate at which molecules are reversed in an electric field than ferroelectric liquid crystals having a small spontaneous polarization value among the compounds of the formula (I) of the present invention, particularly those of the formula (I) wherein l=0, have a spontaneous polarization value as shown in Table 2 amounting to about 300 nC/cm$^2$, whereas, for example, the spontaneous polarization value of a compound $$(+)\ C_2H_5\overset{CH_3}{\underset{*}{C}}HCH_2-\phantom{}\bigcirc-\bigcirc-COO-\bigcirc-OC_8H_{17}$$

disclosed in Japanese patent application laid-open No. Sho 53-22883/1978 is about 1 nC/cm$^2$. In view of the fact, it can be said that the substances of the present invention have an extremely large spontaneous polarization value.

The reason is presumed to be in that the substituent perpendicular to the major axis of the molecule and having a large permanent dipole moment i.e. cyano group is present at a position very close to the asymmetrical carbon atom and the interaction therebetween induce the large spontaneous polarization; thus it can be said that there is a notable difference in the spontaneous polarization value between compounds having the above-mentioned substituent and compounds having the asymmetrical carbon atom at a position apart from a permanent dipole moment or those substituted by fluorine atom, chlorine atom, bromine atom or the like having a far less dipole moment.

In short, such a large spontaneous polarization value is due to the following skeleton, o-cyano-1-methylalkoxybenzene:

$$C_mH_{2m+1}\overset{CH_3}{\underset{*}{C}}HO-\bigcirc^{CN}$$

and it can be said that any of liquid crystal compounds containing such a skeleton are superior ferroelectric liquid crystal materials having a large spontaneous polarization value.

However, compounds of the formula (I) wherein l is one or more do not exhibit such a large spontaneous polarization value since the cyano group is apart from the asymmetrical carbon. On the other hand, for example, a compound of No. 14

$$(S)\ C_6H_{13}\overset{CH_3}{\underset{*}{C}}HO-\bigcirc^{CN}-\bigcirc-COO-\bigcirc-C_8H_{17}$$

has no SC* phase, whereas a compound of No. 59

$$(S)\ C_2H_5\overset{CH_3}{\underset{*}{C}}H(CH_2)_7O-\bigcirc^{CN}-\bigcirc-COO-\bigcirc-C_8H_{17}$$

has SC* phase within a preferred temperature range of

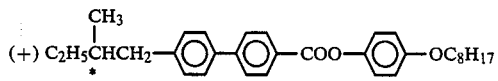

this compound can be said to be a very excellent compound as a component of ferroelectric liquid crystal compositions.

Now, while it is possible to constitute liquid crystal compositions using the compounds of the formula (I), it is also possible to prepare chiral smectic liquid crystal compositions by mixing the compounds of the formula (I) with other smectic liquid crystal compositions. For example, when a compound of the formula (I) is added in a suitable quantity to a smectic C liquid crystal composition, it is possible to prepare a liquid crystal compound exhibiting chiral smectic C phase.

In this case, examples of materials for smectic C liquid crystal compositions are 5-alkyl-2-(4'-alkoxyphenyl)-pyrimidine compounds represented by
5-octyl-2-(4'-octyloxyphenyl)-pyrimidine,
5-octyl-2-(4'-octyloxyphenyl)-pyrimidine,
5-octyl-2-(4'-decyloxyphenyl)-pyrimidine, etc.,
5-alkyl-2-(4'-alkoxyphenyl)-pyridine compounds represented by
5-heptyl-2-(4'-octyloxyphenyl)-pyridine,
5-octyl-2-(4'-octyloxyphenyl)-pyridine,
5-heptyl-2-(4'-nonyloxyphenyl)-pyridine,
5-nonyl-2-(4'-nonyloxyphenyl)-pyridine, etc., 4-alkoxyphenyl-4-alkoxy-benzoate compounds
represented by
4-octyloxyphenyl-4-octyloxy-benzoate,
4-nonyloxyphenyl-4-octyloxy-benzoate,
4-decyloxyphenyl-4-nonyloxy-benzoate, etc.

In addition, the compounds of formula (I) have an optically active carbon; hence when the compound is added to nematic liquid crystals, it has a capability of inducing a twisted structure. Since the nematic liquid crystals i.e. chiral nematic liquid crystals do not form the so-called reverse domain (reverse domain dechiralization lines) of TN mode display elements, the compounds of the formula (I) are usable as an agent for preventing the reverse domain.

(PREPARATION OF THE COMPOUNDS)

Next, a process for preparing the compound of the formula (I) will be described. The compounds of the formula (I) are suitably prepared by the following passageways:

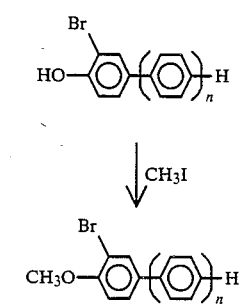

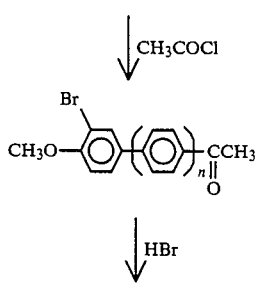

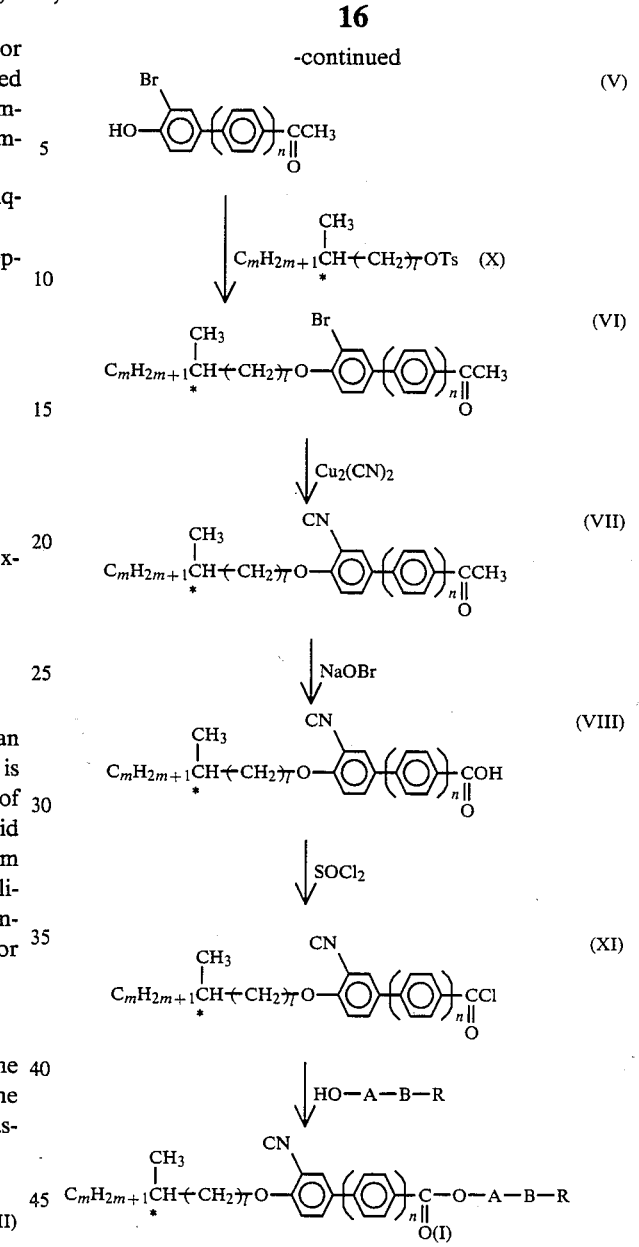

wherein l, m, n, *, R, A and B are as defined above, respectively and Ts represents a p-toluenesulfonyl group

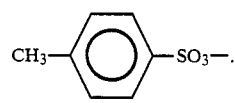.

Namely, o-bromophenol or 3-bromo-4-hydroxybiphenyl (II) each as a known substance is subjected to methyl etherification into a compound (III), which is then reacted with an acid halide such as acetyl chloride to obtain a compound (IV), which is further reacted with hydrobromic acid for demethylation to obtain a compound (V). This compound (V) may also be prepared by directly acetylizing the compound (II) according to a process as described in Example 3. The compound (V) is reacted with an alkyl tosylate as shown by a compound (X) to obtain a compound (VI), which is then reacted with a cyanogenating agent such as cuprous cyanide to obtain a compound (VII). This compound (VII) is oxidized into a compound (VIII), which is reacted with a halogenating agent such as thionyl chloride to obtain an acid halide (IX). The compound (IX) is reacted with a phenol (XI) such as p-alkylphenols, p-alkoxyphenols, 4'-alkyl-4-phenylphenols, 4'-alkoxy-4-phenylphenols, etc. to obtain the objection compound (I).

In the above equations, preparation of the compound (VIII) is substantially important, since preparation passageways from the compound (VIII) into the compound (I) are a mere esterification reaction. The compound (VIII) may be also prepared from the compound (VI) through the following passageways:

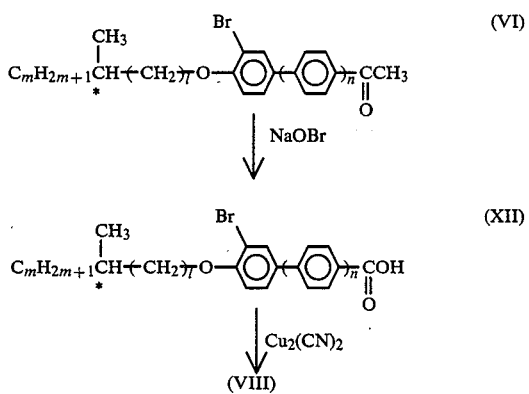

The optically active liquid crystalline compound of the present invention will be described in more detail by way of Examples.

EXAMPLE 1

Preparation of optically active 4'-hexyloxy-4-biphenylyl 3-cyano-4-(1-methylheptyloxy)-benzoate (Preparation of a compound of the formula (I) wherein l=0, m=6, R=—OC$_6$H$_{13}$, A = —⟨O⟩—, B = —⟨O⟩— and n = 0; compound No. 7)

Step 1

KOH (78.0 g, 1.39 mol) was added to O-bromophenol (200 g, 1.16 mol) dissolved in ethanol (700 ml), followed by dropwise adding methyl iodide (197.3 g, 1.39 mol) to the solution, thereafter refluxing the mixture for one hour, distilling off ethanol (400 ml), dissolving the residue in toluene, sufficiently washing the solution with 2N-NaOH aqueous solution, further washing it with water, drying over anhydrous magnesium sulfate, distilling off toluene and distilling the residue under reduced pressure to obtain o-bromoanisole (195.6 g, b.p. 73°~76° C. (4 mmHg)).

Step 2

The above product (100 g, 0.53 mol) was dissolved in carbon disulfide (220 ml), followed by adding anhydrous aluminum chloride to the solution, dropwise adding acetic anhydride to the mixture at a temperature of 0° C. or lower, further refluxing the mixture for 2 hours, further pouring the resulting material in 6N-HCl aqueous solution (1 l), collecting deposited crystals and recrystallizing from ethanol (200 ml) to obtain 3-bromo-4-methoxyacetophenone (84.1 g) (m.p.: 83.1°~84.0° C.).

Step 3

To the above product (84.1 g, 0.367 mol) were added acetic acid (700 ml) and then hydrobromic acid (300 g), followed by refluxing the mixture for 50 hours, thereafter adding water (1 l) and collecting deposited crystals to obtain 3-bromo-4-hydroxyacetophenone (74.6 g) (m.p.: 111.2°~113.0° C.).

Step 4

The above product (45.0 g, 0.21 mol) was dissolved in ethanol (450 ml), followed by adding KOH (23.5 g, 0.42 mol) and then optically active 1-methylheptyl p-toluenesulfonate (71.7 g, 0.25 mol), refluxing the mixture for 6 hours, distilling off ethanol (300 ml), adding toluene, sufficiently washing the resulting material with 2N-NaOH aqueous solution and then water and distilling off toluene to obtain 3-bromo-4-(1-methylheptyloxy)-acetophenone (24.9 g).

Step 5

The above product (20.0 g, 0.06 mol) was dissolved in N-methyl-2-pyrrolidone (80 ml), followed by adding cuprous cyanide (10.8 g, 0.06 mol) to the solution, refluxing the mixture for 9 hours, adding a solution obtained by adding water (40 ml) and conc. hydrochloric acid (6.0 ml) to ferric chloride (24.0 g), further heating the mixture for 2 hours, allowing it to cool down, adding chloroform, agitating the mixture, sufficiently washing the organic layer with water and distilling off the solvent to obtain 3-cyano-4-(1-methylheptyloxy)-acetophenone (11.5 g).

Step 6

The above product (10.0 g, 0.037 mol) was dissolved in 1,4-dioxane (30 ml), followed by dropwise adding a solution prepared in advance by adding bromine (22.0 g) to 20% NaOH aqueous solution (114 ml), at a temperature of 15° C. or lower, further keeping the mixture at 40° C. for 2 hours, acidifying it with hydrochloric acid under cooling, collecting deposited crystals and recrystallizing from n-heptane to obtain 3-cyano-4-(1-methylheptyloxy)-benzoic acid (7.1 g, m.p.: 98.1°~99.9° C.).

Steps 7 and 8

The above product was treated with thionyl chloride in a conventional manner to obtain an acid chloride (5.0 g, 0.018 mol), which was added to a solution of 4'-hexyloxy-4-phenylphenol (5.7 g, 0.020 mol) in pyridine (30 ml) under ice cooling, followed by keeping the mixture at 50°~60° C. for 2 hours, allowing it to cool down, adding toluene, agitating the mixture, washing the organic layer with 6N-HCl aqueous solution and then with 2N-NaOH aqueous solution and further with water, distilling off toluene and recrystallizing the residue from ethanol to obtain optically active 4'-hexyloxy-4-biphenylyl 3-cyano-4-(1-methylheptyloxy)-benzoate (5.1 g). Its phase transition points were as follows:

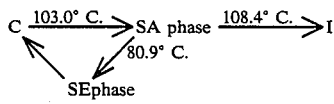

EXAMPLE 2

Preparation of optically active 4'-octyl-4-biphenylyl 3-cyano-4-(1-methylheptyloxy)-benzoate (a compound of the formula (I) wherein l=0, m=6, R=—$C_8H_{17}$,

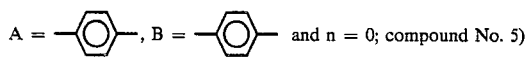 and n = 0; compound No. 5)

3-Cyano-4-(1-methylheptyloxy)-benzoic acid chloride (5.0 g, 0.018 mol) prepared in Example 1 was added to a solution of 4'-octyl-4-phenylphenol (5.6 g, 0.020 mol) dissolved in pyridine (30 ml) under ice cooling, followed by keeping the mixture at 50°~60° C. for 2 hours, allowing it to cool down, adding toluene, agitating the mixture, washing the organic layer with 6N-HCl aqueous solution, then with 2N-NaOH aqueous solution and further with water, distilling off toluene and recrystallizing the residue from ethanol to obtain optically active 4'-octyl-4-biphenylyl 3-cyano-4-(1-methylheptyloxy)-benzoate. Its phase transition points were as follows:

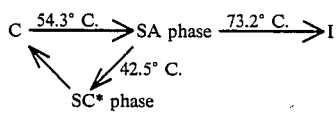

EXAMPLE 3

Preparation of optically active S 4'-octyloxy-phenyl 3'-cyano-4'-(1-methylheptyloxy)-biphenyl-4-carboxylate (a compound of the formula (I) wherein l=0, m=6, R=$OC_8H_{17}$,

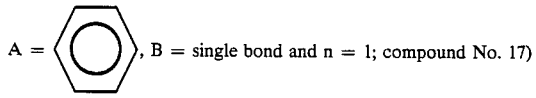, B = single bond and n = 1; compound No. 17)

Step 1
3'-Bromo-4'-hydroxy-4-hydroxy-4-acetylbiphenyl ((V), n=1)

A solution of 3-bromo-4-hydroxybiphenyl (124.5 g, m.p. 96° C.) in carbon disulfide (650 ml) was added over 15 minutes to aluminum chloride (135 g) on an iced water bath. The mixture was then gently boiled under reflux, followed by adding acetyl chloride (79 g) over 40 minutes, refluxing the mixture for further 5 hours, cooling in an ice bath, treating the reaction mixture with water (400 ml), distilling off carbon disulfide on a boiling water bath, collecting solid residue by suction and recrystallizing from ethanol to obtain 3'-bromo-4'-acetoxy-4-acetylbiphenyl (77 g, m.p. 100°~100.5° C.).

Alkaline hydrolysis of the above acetate (76.7 g) gave 3'-bromo-4'-hydroxy-4-acetylbiphenyl (47 g, m.p. 165.5°~170° C. (from ethanol)).

Step 2
S 3'-bromo-4'-(1-methylheptyloxy)-4-acetylbiphenyl ((VI), l=0, m=6, n=1)

The above 3'-bromo-4'-hydroxy-4-acetylbiphenyl (200 g) was treated with 1.2 times equivalents of R 1-methylheptyl p-toluenesulfonate and potassium hydroxide in 97% ethanol (1 l) for 6 hours under reflux. The reaction mixture was worked up in a usual way to obtain crude oily 3'-bromo-4'-(1-methylheptyloxy)-4-acetylbiphenyl (163 g).

Step 3
S 3'-bromo-4'-(1-methylheptyloxy)-4-biphenyl-carboxylic acid ((XII), l=0, m=6, n=1)

An aqueous sodium hypobromate solution prepared from NaOH (102 g), $Br_2$ (117 g) and water (500 ml) was added over 30 minutes to the above ketone (82 g) dissolved in p-dioxane (100 ml) at 15°~20° C., followed by keeping the mixture at 50° C. for 2 hours, treating with sodium bisulfite to destroy the excess of the oxidant. The carboxylic acid precipitated by acidification with 6N hydrochloric acid was recrystallized from acetic acid to obtain S 3'-bromo-4'-(6-methyloctyloxy)-4-biphenylcarboxylic acid (46 g) (C-S, 97.5° C., S-I, 137.3° C.).

Step 4
S 3'-cyano-4'-(1-methylheptyloxy)-4-biphenylcarboxylic acid ((VIII), l=0, m=6, n=1)

A mixture of S 3'-bromo-4'-(1-methylheptyloxy)-4-biphenylcarboxylic acid (56.7 g), cuprous cyanide (16.3 g) and dimethylformamide (140 ml) was heated for 12 hours under reflux, followed by cooling the resulting material to room temperature, treating with 10 wt. % ethylenediamine aqueous solution (700 ml), acidifying with 6N hydrochloric acid, collecting the precipitates by filtration, washing with boiling water, dry-sucking and recrystallizing from acetic acid to obtain S 3'-cyano-4'-(1-methylheptyloxy)-4-biphenylcarboxylic acid (40.8 g) (C-S, 100.0° C., S-I, 138.7° C.).

Other optically active 3'-cyano-4'-(alkoxy)-4-biphenylcarboxylic acids were prepared in a similar way.

Step 5
. Reparation of the title compound

Usual esterification with p-octyloxyphenol, as in Example 2 above, and recrystallization from ethyl acetic - ethyl alcohol gave the title compound. Its phase transition points were as follows: C-SC*: 27.5° C., SC*-SA: 57.0° C., SA-I: 94.3° C., as shown in the Table 1.

EXAMPLE 4 (USE EXAMPLE 1)

A liquid crystal composition 1 consisting of the following components and having a SC* phase having a spontaneous polarization value of 1 $nC/cm^2$ or less was prepared:

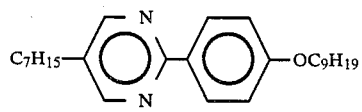  6.25 wt. %

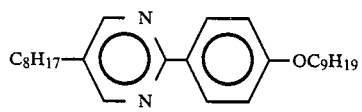  12.5 wt. %

-continued

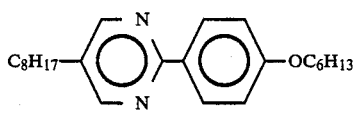  21.88 wt. %

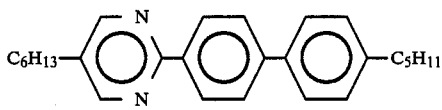  12.5 wt. %

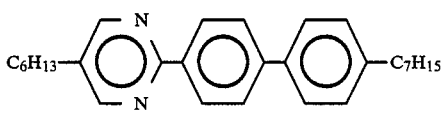  9.38 wt. %

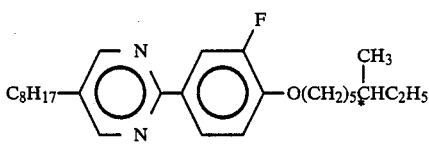  18.75 wt. %

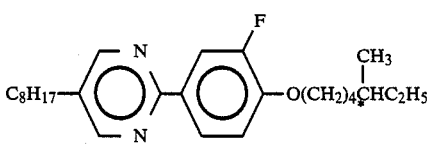  12.25 wt. %

  6.25 wt. %

The phase transition points of this composition are as follows:

This composition was filled in a cell 2 μm thick provided with transparent electrodes each obtained by applying PVA as an aligning agent thereonto and rubbing the resulting surface to subject it to parallel aligning treatment, followed by placing the resulting cell between two sheets of crossed polarizers and impressing a square wave having a wave height of 10 V. As a result, the change in the intensity of transmitted light was observed. Its response time was sought from the change in the intensity of transmitted light at that time to give a value of about 3 μ sec at 25° C.

To this composition was added a compound of the present invention (compound No. 7) in 20% by weight. The resulting liquid crystal composition 2 had the following phase transition points:

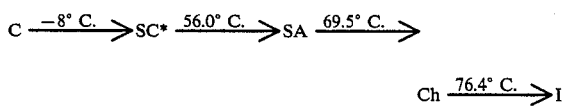

And its spontaneous polarization value at 25° C. was 9.9 nC/cm² and its tilt angle was 20.5°. The response time of this composition was sought in the same manner as in the case of the composition 1 to give 220 μ sec.

As seen from the above results, use of the compound of the present invention notably improved the response time.

EXAMPLE 5 (USE EXAMPLE 2)

To the liquid crystal composition 1 of Example 4 was added a compound of Example 2 of the present invention (compound No. 5) in 20% by weight. The resulting liquid crystal composition 3 had the following phase transition points:

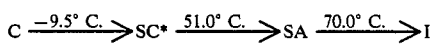

Its spontaneous polarization value at 25° C. was 10.6 nC/cm² and its tilt angle was 20°.

This composition 3 was filled in a cell 2 μm thick provided with transparent electrodes each obtained by applying PVA as an aligning agent thereonto and rubbing the resulting surface to subject it to parallel aligning treatment, followed by placing the resulting cell between two sheets of crossed polarizers and impressing a square wave having a wave height of 10 V. As a result, the change in the intensity of transmitted light was observed. Its response time was sought from the change in the intensity of transmitted light at that time to give a value of 210 μ sec at 25° C.

As seen from the above results, when the compound of the present invention was used, a chiral smectic liquid crystal composition having a high response rate was obtained.

EXAMPLE 6 (USE EXAMPLE 3)

A composition consisting of the following components and being an achiral substance and having SC phase:

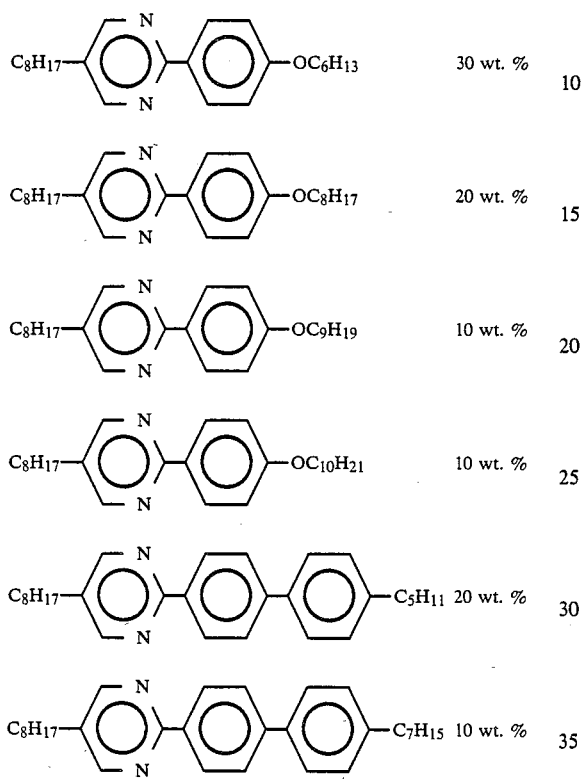

This composition had the following phase transition points:

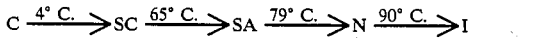

To this composition was added a compound of Example 1 of the present invention (compound No. 7) in 20% by weight. As a result, a SC* phase exhibiting ferroelectric property within a temperature range of 8° to 70° C. was observed. The spontaneous polarization value at 25° C. of this composition was 8.0 nC/cm² and its tilt angle was 20°.

This composition was filled in a cell of 2 μm thick provided with transparent electrodes each obtained by applying PVA as an aligning agent thereonto and rubbing the resulting surface to subject it to parallel aligning treatment, followed by placing the resulting cell between two sheets of crossed polarizers and impressing a square wave having a wave height of 10 V. As a result, change in the intensity of transmitted light was observed. Its response time was sought from the change in the intensity of transmitted light at that time to give a value of 270 μ sec.

As seen from the above results, when the compound of the present invention was added to a compound (or composition) having a SC phase exhibiting no ferroelectric property, a ferroelectric liquid crystal composition exhibiting a very high rate response property was obtained.

COMPARATIVE EXAMPLE

To the liquid crystal composition 1 Example 4 was added the following compound of a structure having CN group of the compound of the present invention replaced by F atom in 20% by weight:

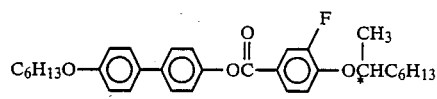

to obtain a liquid crystal composition. Its phase transition points were as follows:

This composition had a spontaneous polarization value at 25° C. of 1.7 nC/cm² and a tilt angle of 26°.

Its response time was sought in the same manner as in the case of Example 4 to give a value of 860 μ sec i.e. about 4 times the value in the case of the composition 1.

As seen from the above results, addition of the compound of the present invention having cyano group at a position very close to the asymmetrical carbon exhibits a notable effectiveness in the aspect of the response time as compared with addition of other similar compounds.

EXAMPLE 7 (USE EXAMPLE 4)

A nematic liquid crystal composition consisting of

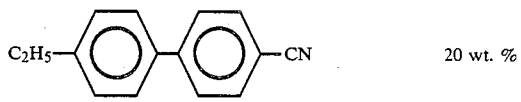

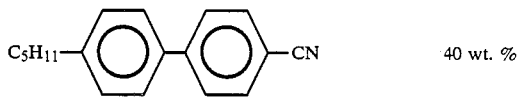

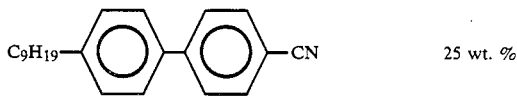

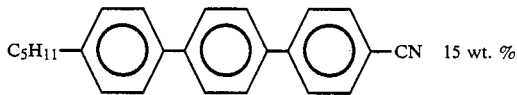

was filled in a cell provided with transparent electrodes each obtained by applying polyvinyl alcohol (PVA) thereonto and rubbing the resulting surface to subject it to a parallel aligning treatment and having a distance between the electrodes of 10 μm to prepare a TN mode cell. This cell was observed under a polarizing microscope. As a result, formation of a reverse twist domain was observed. When a compound of Example 2 of the present invention was added in 0.1% by weight to this TN mode cell, it was observed that the reverse twist domain dissolved and a uniform nematic phase was observed.

What we claim is:

1. An optically active liquid crystalline compound expressed by the formula

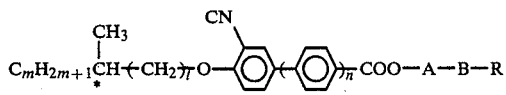 (I)

wherein m represents an integer of 2 to 18; l represents an integer of 0 to 12; n represents 0 to 1; R represents an alkyl group or an alkoxy group each of 2 to 20 carbon atoms, a halogen atom or a cyano group; A represents a single bond,

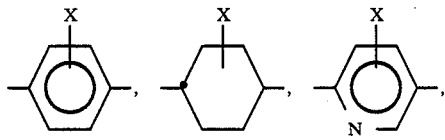

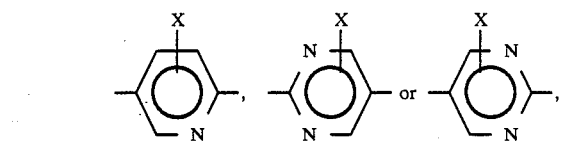

and B represents

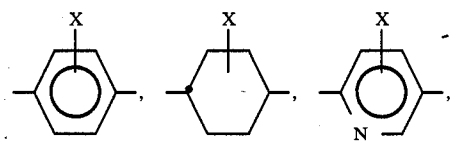

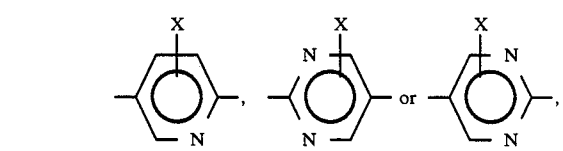

wherein X represents a hydrogen atom, a halogen atom or a cyano group.

2. An optically active liquid crystal compound according to claim 1 wherein said l in the formula (I) represents zero.

3. An optically active liquid crystal compound according to claim 1 wherein said l in the formula (I) represents 1 to 7.

4. An optically active liquid crystal compound according to claim 1 wherein said m in the formula (I) represents an integer of 2 to 6.

5. A chiral smectic liquid crystal composition comprising at least two components at least one of which is an optically active liquid crystalline compound as set forth in claim 1.

6. A light switching element comprising a chiral smectic liquid crystal composition as set forth in claim 5.

7. An optically active liquid crystalline compound according to claim 1 wherein n represents 1, R represents the alkyl group or alkoxy group, —A—B—represents

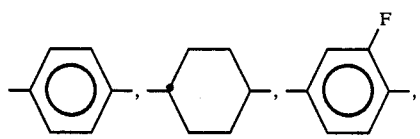

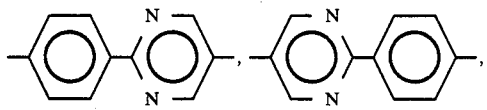

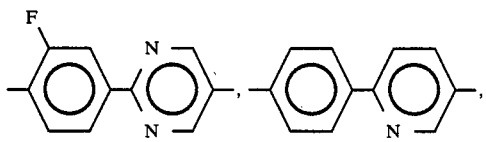

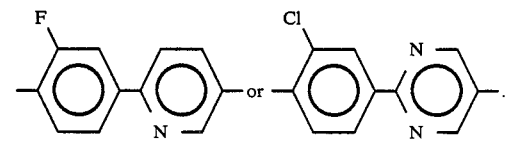

8. An optically active liquid crystalline compound according to claim 7 wherein —A—B—represents

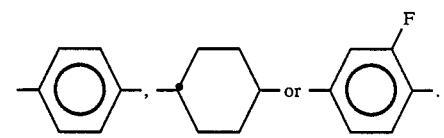

9. An optically active liquid crystalline compound according to claim 7 wherein —A—B—represents

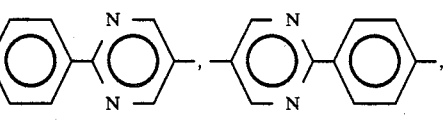

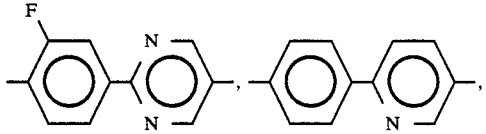

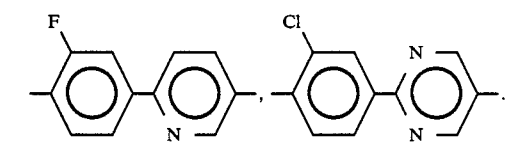

10. An optically active liquid crystalline compound according to claim 1 wherein n represents 0, R represents the alkyl group or alkoxy group, —A—B—represents

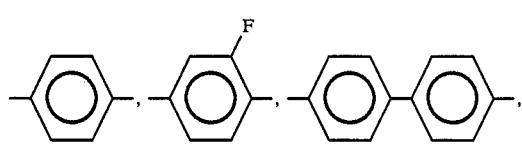

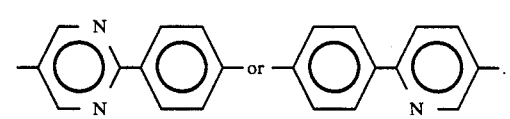

11. An optically active liquid crystalline compound according to claim 10 wherein —A—B—represents

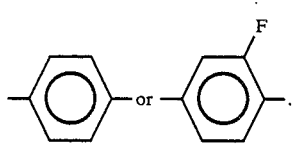
12. An optically active liquid crystalline compound according to claim 10 wherein —A—B—represents
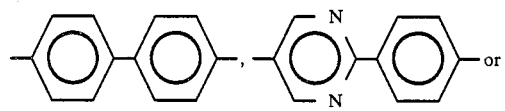
13. An optically active liquid crystalline compound according to claim 7 wherein R represents the alkoxy group and —A—B—represents
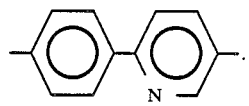
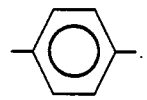
* * * * *